United States Patent [19]

Blow et al.

[11] Plant 4,242

[45] Apr. 18, 1978

[54] DOGWOOD TREE — IMPERIAL WHITE VARIETY

[76] Inventors: Elizabeth Parris Blow, 911 Westwood Dr., Raleigh, N.C. 27607; Muriel Fiscus Steppe, 3800 New Bern Ave., Raleigh, N.C. 27610

[21] Appl. No.: 762,120

[22] Filed: Jan. 24, 1977

[51] Int. Cl.[2] ..... A01H 5/00

[52] U.S. Cl. ..... Plt./51

[58] Field of Search ..... Plt./51

[56] References Cited

U.S. PATENT DOCUMENTS

P.P. 442 1/1941 Owens ..... Plt./51

P.P. 2,112 12/1961 Chase ..... Plt./51

*Primary Examiner*—Robert E. Bagwill

*Attorney, Agent, or Firm*—Burns, Doane, Swecker & Mathis

[57] ABSTRACT

A new and distinct variety of white Flowering Dogwood, botanically known as *Cornus florida* is provided. The new variety most nearly resembles the native Flowering Dogwood and is distinguished therefrom by (1) the unusually large size of the solid white bracts which appear adjacent the flowers, (2) the unusually large size of the leaves, (3) a more vigorous and a more spreading growth habit, and (4) an improved drought tolerance.

3 Drawing Figures

SUMMARY OF THE INVENTION

The new and distinct variety of Flowering Dogwood (*Cornus florida*) was discovered and recognized to be a new variety in the Spring of 1975 while growing in a cultivated boxwood bed at 911 Westwood Dr., Raleigh, N.C. 27607. The parentage of the new variety is unknown. Since other native Flowering Dogwood trees were growing in the area, it is possible that the new variety may be a chance seedling resulting from seed produced on these trees. Also, there is a possibility that the seed of unknown origin which produced the new variety may inadvertently have been transported to the cultivated area where the new variety appeared when the adjacent boxwood plants were transplanted to the area.

Our discovery differs from the native white Flowering Dogwood by, inter alia, the following combination of characteristics:

1. the unusually large size of the solid white bracts which appear adjacent the flowers,
2. the unusually large size of the leaves,
3. a more vigorous and a more spreading growth habit, and
4. an improved drought tolerance.

The new variety as a young seedling has undergone temperatures as low as −5° F. with no apparent damage.

Because of the distinctive characteristics of the new variety the plant was asexually reproduced by rooted cuttings at Raleigh, N.C. The progeny bloomed in the Spring of 1976, and it has been demonstrated that the unique combination of characteristics comes true to form and is established and transmitted through succeeding propagation.

BRIEF DESCRIPTION OF THE DRAWINGS

The accompanying drawings show typical specimens of the new variety.

DETAILED DESCRIPTION OF THE NEW VARIETY

Figure 1:
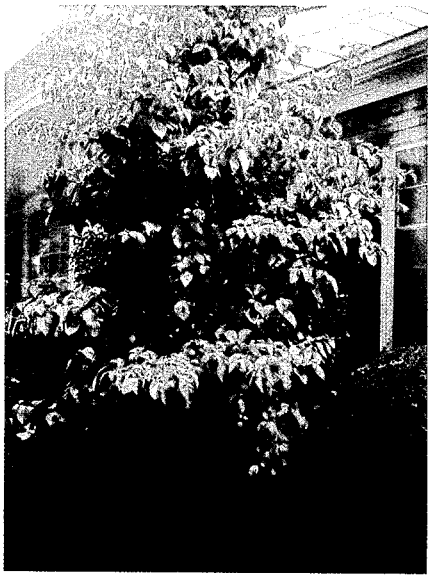
FIG. 1 illustrates the unusually large size of the leaves of the new variety during the summer months.
Figure 2:
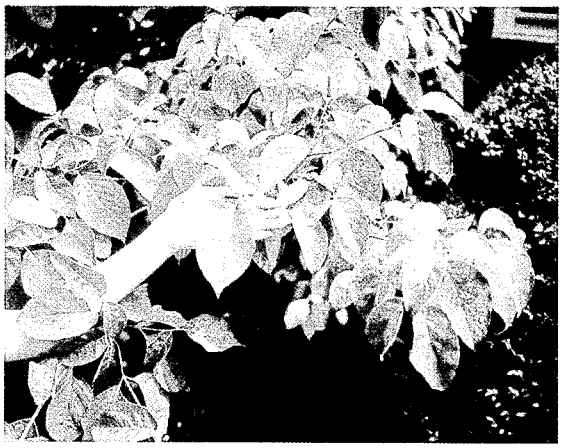
FIG. 2 illustrates the overall growth habit of the original tree of the new variety during the summer at an age of approximately 7 years.
Figure 3:
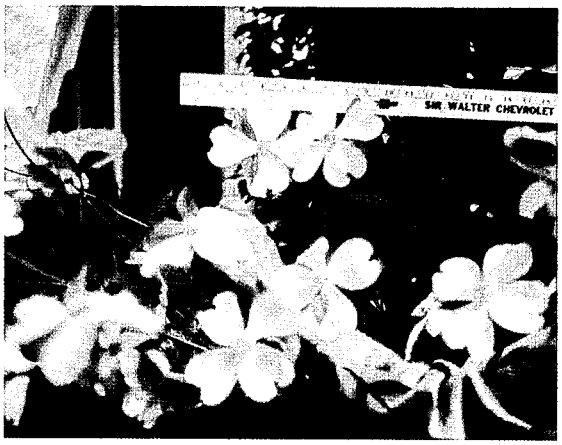
FIG. 3 illustrates the unusually large size of the four solid white bracts of the new variety.

The following description was made from plants growing at Raleigh, N.C. Color terminology employed is to be accorded its ordinary dictionary significance. Unless otherwise stated the new variety has characteristics substantially similar to those of the native Flowering Dogwood.

Growth habit: Extremely vigorous as a young tree with new growth often achieving a length of 24 inches annually. The branching habit is more spreading than that of the native Flowering Dogwood, but less spreading than that of the Cloud 9 variety (i.e. U.S. Plant Pat. No. 2,112). Accordingly, the new variety has a more upright growth habit than the Cloud 9 variety.

Leaves: Opposite; simple; deciduous; unusually large size up to approximately 7¼ inches in length and up to approximately 5 inches in width; ovate, entire; arcuately veined; absence of hair; bright green above; paler green beneath; turning brilliant copper red in the autumn. The leaf color during the summer appears to be identical to that of the native Flowering Dogwood. The leaves of the native Flowering Dogwood and of the Cloud 9 variety growing in the same area are smaller. For instance, the leaves of the Cloud 9 variety commonly are up to 6 inches in length and up to 4 inches in width. The unusually large leaves of the present variety tend to give the tree a "magnolia-like" appearance overall.

Flowers: Surrounded by four unusually large solid white bracts giving the impression of one large flower having a diameter of approximately 4½ to 5½ inches; occasionally the bracts give the impression of a flower having a diameter of 6 inches. The large white bracts are obovate in shape, notched at the apex, and form at the same time as the leaves. The bracts appear at the same time as those of the native Flowering Dogwood; however, the bracts of the native Flowering Dogwood trees in the area are substantially smaller. Additionally, the bracts of the present variety generally are larger than those of the Cloud 9 variety which commonly give the impression of flowers having a diameter of up to approximately 4 to 4½ inches. For each variety the individual bract lengths are approximately one-half of the specified flower diameters. Also the bract shape of the present variety tends to be different in at least some respects than that of the Cloud 9 variety and more closely resembles that of the native white Flowering Dogwood with one opposite pair of bracts having a broader more rounded base than the other opposite bract pair which tends to possess a substantially non-rounded and narrower base. Conversely all four bracts of the Cloud 9 variety tend to be more uniform in shape and to possess a base of the broader more rounded configuration. The flowers of the new variety lack any appreciable fragrance.

Silvical character: The variety appears to be more drought tolerant than other native Flowering Dogwood trees growing in the immediate area.

The new and distinct variety has been named the Imperial White variety.

We claim:

1. A new and distinct variety of white Flowering Dogwood tree, botanically known as *Cornus florida,* substantially as illustrated and described, characterized particularly as to novelty by the unique combination of (1) the unusually large size of solid white bracts which appear adjacent the flowers, (2) the unusually large size of the leaves, (3) a more vigorous and a more spreading growth habit, and (4) an improved drought tolerance.

* * * * *